(12) United States Patent
Wang et al.

(10) Patent No.: US 11,324,544 B2
(45) Date of Patent: May 10, 2022

(54) MEDICAL INSTRUMENT

(71) Applicant: GYRUS ACMI, INC., Southborough, MA (US)

(72) Inventors: Huisun Wang, Maple Grove, MN (US); Kester J. Batchelor, Mound, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 581 days.

(21) Appl. No.: 16/045,317

(22) Filed: Jul. 25, 2018

(65) Prior Publication Data
US 2020/0030020 A1 Jan. 30, 2020

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1482* (2013.01); *A61B 2018/0063* (2013.01); *A61B 2018/00595* (2013.01); *A61B 2018/00601* (2013.01); *A61B 2018/126* (2013.01); *A61B 2018/1455* (2013.01); *A61B 2018/1462* (2013.01)

(58) Field of Classification Search
CPC ............ A61B 18/1445; A61B 18/1482; A61B 2018/0063; A61B 2018/00601; A61B 2018/00607; A61B 2018/1445
See application file for complete search history.

(56) References Cited

U.S. PATENT DOCUMENTS

| | | |
|---|---|---|
| 763,226 A | 6/1904 | Frederick |
| 3,503,396 A | 3/1970 | Pierie et al. |
| 4,642,090 A | 2/1987 | Utrata |
| 5,728,121 A | 3/1998 | Bimbo et al. |
| 5,752,973 A | 5/1998 | Kieturakis |
| 5,754,928 A | 5/1998 | Moe et al. |
| 6,086,586 A | 7/2000 | Hooven |
| 6,123,701 A | 9/2000 | Nezhat |
| 6,270,497 B1 | 8/2001 | Sekino et al. |
| 6,406,485 B1 | 6/2002 | Hossain et al. |
| 6,942,676 B2 | 9/2005 | Buelna |
| 7,182,775 B2 | 2/2007 | De Guillebon |
| 7,276,068 B2 | 10/2007 | Johnson et al. |
| 7,491,202 B2 | 2/2009 | Odom et al. |

(Continued)

FOREIGN PATENT DOCUMENTS

| | | |
|---|---|---|
| EP | 2092905 A1 | 8/2009 |
| EP | 2353534 A1 | 8/2011 |

(Continued)

*Primary Examiner* — Linda C Dvorak
*Assistant Examiner* — Ryan T Clark
(74) *Attorney, Agent, or Firm* — Schwegman Lundberg & Woessner, P.A.

(57) ABSTRACT

A jaw assembly that includes a first jaw and a second jaw. The first jaw includes a first outer jaw member having an effecting surface; a first inner jaw member having an effecting surface; and an element connecting the first outer jaw member and the first inner jaw member. The first inner jaw member is moveable relative to the first outer jaw member. The effecting surface of the first outer jaw member is proud of the effecting surface of the first inner jaw member in a direction of the second jaw.

20 Claims, 4 Drawing Sheets

(56) References Cited

U.S. PATENT DOCUMENTS

| | | |
|---|---|---|
| 8,192,433 B2 | 6/2012 | Johnson et al. |
| 8,262,655 B2 | 9/2012 | Ghabrial et al. |
| 8,298,232 B2 | 10/2012 | Unger |
| 8,317,787 B2 | 11/2012 | Hanna |
| 8,382,754 B2 | 2/2013 | Odom et al. |
| 8,597,297 B2 | 12/2013 | Couture et al. |
| 8,647,343 B2 | 2/2014 | Chojin et al. |
| 8,795,274 B2 | 8/2014 | Hanna |
| 8,945,125 B2 | 2/2015 | Schechter et al. |
| 8,968,308 B2 | 3/2015 | Horner et al. |
| 2002/0188294 A1 | 12/2002 | Couture et al. |
| 2003/0171748 A1 | 9/2003 | Truckai et al. |
| 2005/0203507 A1 | 9/2005 | Truckai et al. |
| 2008/0195093 A1* | 8/2008 | Couture ............ A61B 18/1445 606/45 |
| 2009/0054894 A1 | 2/2009 | Yachi |
| 2009/0149853 A1 | 6/2009 | Shields et al. |
| 2009/0182333 A1 | 7/2009 | Eder et al. |
| 2011/0118736 A1 | 5/2011 | Harper et al. |
| 2011/0184404 A1* | 7/2011 | Walberg ............ A61B 18/1445 606/33 |
| 2011/0319886 A1* | 12/2011 | Chojin ............... A61B 18/1445 606/37 |
| 2013/0014375 A1 | 1/2013 | Hempstead et al. |
| 2014/0155893 A1 | 6/2014 | Chojin et al. |
| 2015/0305796 A1 | 10/2015 | Wang |
| 2017/0348044 A1 | 12/2017 | Wang et al. |

FOREIGN PATENT DOCUMENTS

| | | |
|---|---|---|
| EP | 2353535 A1 | 8/2011 |
| EP | 2554135 A1 | 2/2013 |
| WO | 2007/103986 A2 | 9/2007 |

\* cited by examiner

MEDICAL INSTRUMENT

FIELD

These teachings relate to a medical instrument that is configured to effect an anatomical feature.

BACKGROUND

Forceps are plier-like instruments that include a jaw assembly. The jaw assembly comprises a pair of opposing jaws that are configured to effect an object or anatomical feature. For example, the jaws can be used to grip, capture, grasp, manipulate, pull, constrict, cut, and/or dissect an anatomical feature. Some forceps also include electrosurgical capabilities for electrically effecting (e.g., cutting and/or coagulating) an anatomical with one or more therapy currents.

SUMMARY

A jaw assembly that includes a first jaw and a second jaw. The first jaw includes a first outer jaw member having an effecting surface; a first inner jaw member having an effecting surface; and an element connecting the first outer jaw member and the first inner jaw member. The first inner jaw member is moveable relative to the first outer jaw member. The effecting surface of the first outer jaw member is proud of the effecting surface of the first inner jaw member in a direction of the second jaw.

A method of treating an anatomical feature with a jaw assembly according to any of these teachings. The method includes a step of moving the jaw assembly into a first closed position so that a first gripping force is applied onto the anatomical feature with the effecting surface of the first outer jaw member and the second jaw. The method includes a step of moving a cut blade to cut the anatomical feature and/or deliver a fluid to the anatomical feature. The method includes a step of sequentially moving the jaw assembly into a second closed position so that a second gripping force is applied onto the anatomical feature with the effecting surface of the first inner jaw member and the second jaw.

DETAILED DESCRIPTION

Figure 1:
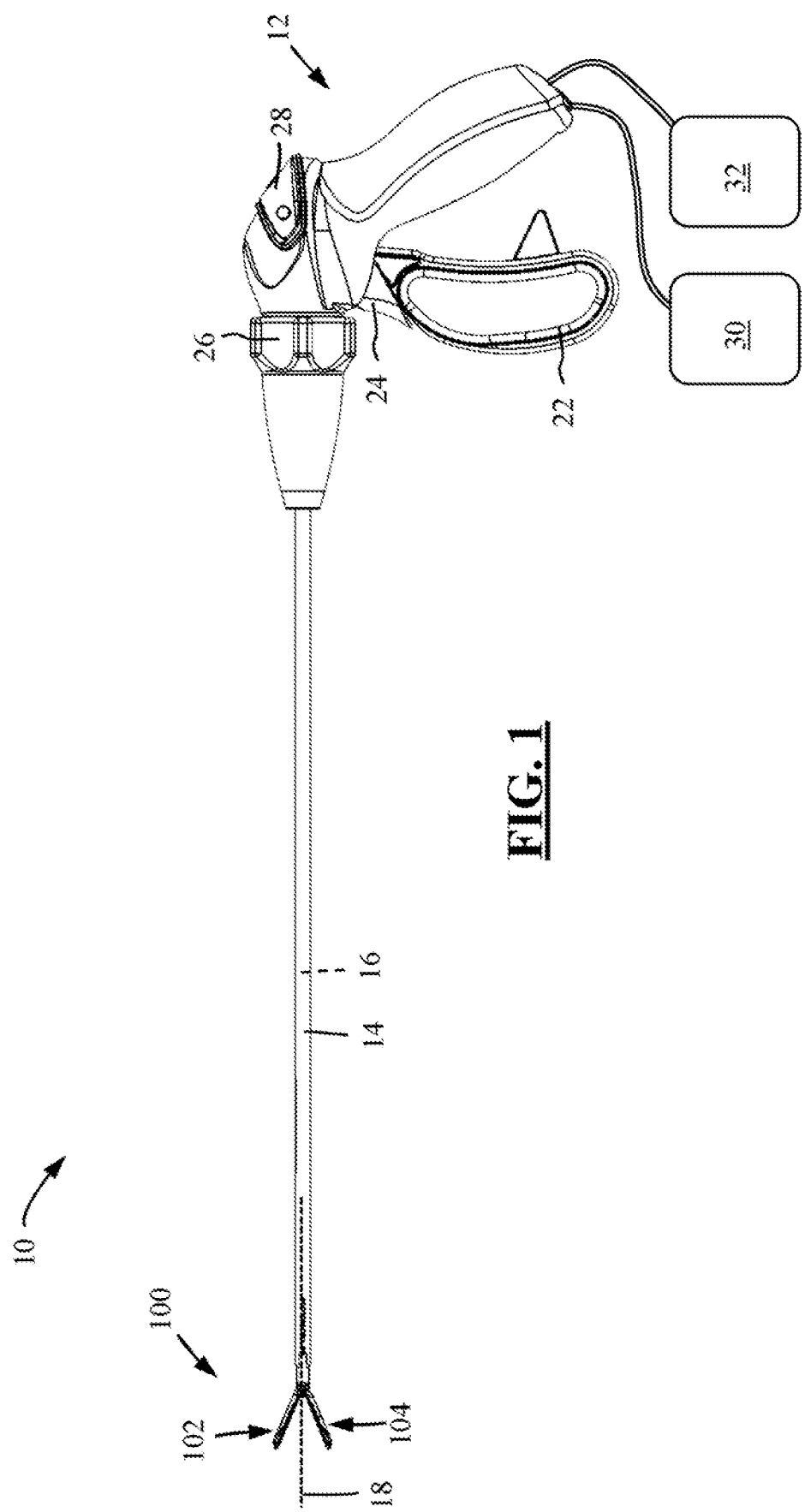
FIG. 1 is side view of a medical instrument.

These teachings disclose an instrument. The instrument can be any instrument for effecting an object or anatomical feature. Effecting may mean, for example: manipulating, engaging, moving, holding, clamping, grasping, gripping, pushing, pulling, cutting, tearing, coagulating, sealing, cauterizing, dissecting, fulgurating an object or anatomical feature. The object may be any object, whether a part of the anatomy or not. When part of the anatomy, the object may be any anatomical feature such as, for example, one or more vessels, tissue, veins, arteries, tumors, the like, or a combination thereof.

The instrument can be used in medically related procedures, in non-medically related procedures, or both. The instrument can be used in open and/or laparoscopic or minimally invasive procedures. The instrument can be forceps, medical forceps, cutting forceps, electrosurgical forceps, bipolar forceps, pincers, tweezers, tongs, pliers, clips, clamps, the like, or a combination thereof.

The instrument may be used with power or without power. When used with power, the instrument can be used in electrosurgery. When used with power, the instrument may be an electrosurgical instrument. The instrument and/or one or more elements of the instrument or jaw assembly can be in electrical communication with a suitable power source so that the instrument or jaw assembly can be used in a bipolar circuit, a monopolar circuit, or both.

The instrument may be in fluid communication with a fluid source. The fluid source may be configured to house, support, store, contain, and/or deliver one or more fluids to the instrument, jaw assembly, cut blade, or a combination thereof.

The fluid source may be located or contained inside the instrument or hand piece. The fluid source may be located a distance away from the instrument or hand piece. The fluid source may be a reservoir, such as a bag or container. The fluid source may be in fluid communication with the jaw assembly. The fluid source may be in fluid communication with the cut blade. The fluid source may be in fluid communication with one or more weep ports. Fluid communication means the fluid source and the element of the instrument or jaw assembly that is configured to receive the fluid is connected via one or more tubes, conduits, passageways, etc. that are configured to transport the fluid from the fluid source to the element. The instrument and/or the fluid source may comprise a pump configured to move or transport the fluid from the source to the element configured to receive the fluid.

The fluid may be a solution of water, saline, collagen, air, fibrin, a tissue adhesive, cyanoacrylate and derivatives, such as, for example, octylcynoacrylate, or a combination thereof in a concentrated or diluted format.

The instrument may comprise a hand piece. The hand piece may function to be held and/or manipulated by a user. The hand piece may function to house, support, and/or contain one or more elements of the instrument. For example, the hand piece may house, support, and/or contain the inner and outer shafts, the jaw assembly, the cut blade, the power source, the fluid source, or a combination thereof. The hand piece may house, support, and/or contain or more elements configured to move or actuate the jaw assembly; the one or more jaws; the cut blade; apply electrosurgical energy or therapy current from the power source; apply fluid from the fluid source; or a combination thereof.

The hand piece may house, support, and/or contain one or more electrical conductors or wires for connecting the jaw assembly, the one or more jaws, the one or more jaw members, the one or more effecting surfaces, the cut blade, or a combination thereof to one or more poles of the power source. The hand piece may house, support, and/or contain one or more tubes or passageways for connecting the jaw assembly and/or cut blade to the fluid source. The hand piece may include one or more electrical plugs and/or ports for connecting the instrument, the one or more jaws, jaw members, effecting surfaces, and/or cut blade to the power source, fluid source, or both.

The instrument and/or the hand piece may comprise one or more user controls. A user control may function to operate or actuate the instrument, the jaw assembly, the cut blade, the power source, the fluid source, or a combination thereof. For example, one or more of the user controls may be pressed, manipulated, moved, repositioned, actuated, etc. to open/close the jaw assembly; move one or both jaws towards or away from each other; rotate the jaw assembly; advance or retract the jaw assembly relative to the hand piece; advance or retract a cut blade relative to the hand piece; rotate the cut blade; apply one or more therapy electrical currents from the power source to one or more elements of the instrument; apply fluid from the fluid source to one or more elements of the instrument; or a combination thereof.

A user control may be one or more: wheels, triggers, levers, buttons, foot pedals, the like, or a combination thereof. For example, manipulation or movement of the lever may be configured to move the jaw assembly (i.e., move one or both of the jaws) from an open configuration to one or more of the closed configurations, and vice versa. For example, manipulation or movement of the wheel may be configured to rotate the jaw assembly and/or the cut blade about a longitudinal axis of the inner and/or outer shafts. For example, manipulation or movement of the trigger may be configured to move, translate, advance, retract, and/or reciprocate the cut blade along a longitudinal axis of the cut blade, inner shaft, and/or outer shaft. For example, manipulation or movement of the button may be configured to apply a therapeutic current or signal from the power supply to the jaw assembly, one or both of the jaws, one or more of the effecting surfaces, the cut blade, or a combination thereof. For example, manipulation or movement of a button or other user control like a foot pedal may be configured to deliver or expel fluid from the fluid source through one or more weep ports in the cut blade, the jaw assembly, or both.

The instrument may comprise an outer shaft. The outer shaft may function to permit a portion of the instrument to be inserted into a patient or the anatomy, while a portion of the instrument remains outside of the patient or anatomy. The outer shaft may be configured and sized to permit insertion into the anatomy through a trocar.

The outer shaft may be a tube or tubular member. The outer shaft may be an elongated member that extends along a longitudinal axis, which may be the same longitudinal axis that the inner shaft and/or the cut blade extend along. The proximal end of the outer shaft may be connected to the hand piece and/or to one or more user controls on the hand piece. The outer shaft may be at least partially hollow and may define therein an inner portion. The hollow or inner portion of the outer shaft may be sufficiently sized so that one or more jaws, a jaw assembly, a cut blade, an inner shaft, or a combination thereof can be received in and/or moved (i.e., linearly or rotationally about the longitudinal axis) inside or within the outer shaft.

The outer shaft may be substantially straight; may include one or more angles, bends or arcs; or a combination thereof. The outer shaft may be substantially rigid, substantially flexible, substantially resilient, or a combination thereof.

In some configurations, the outer shaft may be configured to be moved or is moveable relative to the hand piece. Moveable means that the outer shaft is moveable axially, distally, proximally, rotationally or a combination thereof relative to the hand piece. In such configurations, the outer shaft may be in communication with one or more of the user controls and can be moved by manipulating one of the user controls. For example, by manipulating one or more of the user controls, the outer shaft can be moved a first distance away from the hand piece in a first direction (i.e., distally, in a direction away from the hand piece) so that the outer shaft applies a pressing force onto one or both of the jaws, or more specifically, onto one or both of the inner jaw members, to move or pivot one or both of the jaws into the first closed or gripping configuration. By manipulating one or more of the user controls, the outer shaft can be moved a second distance away from the hand piece in the first direction (i.e., distally, in a direction away from the hand piece) so that the outer shaft applies a pressing force onto one or both of the jaws, or more specifically onto one or both of the inner jaw members, to move or pivot one or both of the jaws into the second closed or gripping configuration. The second distance is longer or farther away from the hand piece than the first distance. In such a configuration, the inner shaft may be fixed to the hand piece or otherwise axially immovable relative to the outer shaft and/or hand piece. Conversely, by manipulating one or more user controls, the outer shaft can be moved in a second direction (i.e., proximally, in a direction towards the hand piece) so that the previously applied pressing force applied onto one or both of the inner jaw members is reduced or eliminated, thus allowing one or both of the jaws to relax or flex or pivot into an open configuration or move or pivot from the second closed configuration into the first closed configuration. The open configuration may be the steady state configuration, which exists when no pressing force is applied onto the inner jaw members. In this type of configuration where the outer shaft is moveable relative to the hand piece, the jaw assembly is preferably fixed to the hand piece and/or the inner shaft and does not move distally or proximally relative to the hand piece or outer shaft. In this configuration, however, the jaw assembly and thus the inner shaft may be configured to rotate about a longitudinal axis of the outer shaft to reposition the jaw assembly and/or cut blade relative to an object or anatomical feature or site of interest.

Alternatively, in some configurations, proximal movement of the outer shaft relative to the hand piece (i.e., movement of outer shaft towards hand piece) may function to move or pivot one or both of the jaws or the jaw assembly into one or both of the closed configurations. Distal movement of the outer shaft relative to the hand piece (i.e., movement of outer shaft away from the hand piece may function to move or pivot one or both of the jaws away from each other so that the jaw assembly is moved into the open configuration.

Alternatively, the outer shaft may be fixed or not moveable relative to the hand piece, and instead the inner shaft may be moveable relative to the hand piece and outer shaft. In such a configuration, by manipulating one or more user controls, the inner shaft can be moved in a first direction (i.e., proximally, in a direction towards the hand piece) so that the outer shaft applies a pressing force onto one or both of the jaws or inner jaw members so that the jaw assembly or one or both of the inner jaw members can be moved or pivoted into one or more of the closed configurations. By manipulating one or more user controls, the inner shaft can be moved in a second direction (i.e., distally, in a direction away the hand piece) so that the previously applied pressing force is reduced or eliminated from the inner jaw members so that the jaw assembly can move into an open configuration.

Alternatively, the jaw assembly may be like tweezers, and the jaws can be manually moved into one or more of the closed configurations by applying a pressing force on one or both of the jaws with a user's fingers. More specifically, the pressing force can be applied onto one or both of the inner jaw members to move the jaw assembly into the first closed configuration, and then additional pressing force applied onto one or both of the inner jaw member functions to move the jaw assembly into the second closed configuration. Releasing the pressing force from one or both of the jaws or one or both of the inner jaw members functions to allow for the jaws to relax into the open configuration or into the first closed configuration from the second closed configuration. In such a configuration, the inner and outer shafts may be omitted from the instrument, and the instrument may comprise only the inner jaw members and outer jaw members.

The instrument may comprise an inner shaft. The inner shaft may be an elongated member that extends along a longitudinal axis, which may be the same axis that the outer shaft and/or the cut blade extend along. The proximal end of the inner shaft may be connected to one or more user controls or to the hand piece. The distal end of the inner shaft may be connected to one or more of the jaws or one or more of the inner jaw members. The distal end of the inner shaft may be connected to one or more of the jaws or one or more of the inner jaw members via one or more pivot joints so that the jaws and/or inner jaw members can pivot or move relative to the inner shaft about the corresponding pivot joint between the open configuration and one or more of the closed configurations.

The inner shaft may be a tube or tubular member. The inner shaft may be at least partially hollow and may define therein an inner portion. The hollow or inner portion of the inner shaft may be sufficiently sized so that a cut blade can be received in and/or moved (i.e., linearly or rotationally about the longitudinal axis) inside the inner shaft.

The inner shaft may be substantially straight; may include one or more angles, bends or arcs; or a combination thereof. The inner shaft may be substantially rigid, substantially flexible, substantially resilient, or a combination thereof. The inner shaft may be coaxial relative to the outer shaft. The axis that the inner shaft extends along may be the same as the axis that the outer shaft and/or cut blade extend along. The axis that the inner shaft extends along may be different (e.g., offset) than the axis that the outer shaft and/or cut blade extend along.

The instrument may comprise one or more cut blades. The cut blade may function to cut an anatomical feature. The cut blade may be a cutting blade or a scalpel. The cut blade may be connected to the power source so that the cut blade can be used to electrically effect an anatomical feature by passing an electrical therapy current to or through the anatomical feature. The cut blade may not be connected to the power source or is electrically isolated from the power source; thus, the cut blade may be free from passing an electrical therapy current to effect an anatomical feature. Thus, the cut blade may be a cold cut blade or a mechanical cut blade.

The cut blade may be located between the opposing first and second jaws; between the opposing inner jaw members; between the opposing outer jaw members; within the inner shaft; within the outer shaft; outside of the inner shaft but inside of the outer shaft; or a combination thereof. The cut blade may be located in between the pivot joints that connected the first and second inner jaw members to the outer shaft. The cut blade may be contained within a slot opening or a blade slot defined in one or both of the inner jaw members, one or both of the outer jaw members, one or both of the jaws, the corresponding effecting surfaces, or a combination thereof. Such a slot opening or blade slot may separate the inner jaw member into two portions, like a left and right side arranged on opposite sides of a plane or axis that extends perpendicular to a longitudinal axis of the inner and outer shaft members.

The cut blade may be moved while the jaw assembly is in the open configuration, the closed configuration, the first closed configuration, the second closed configuration, or a combination thereof. Moved means the cut blade can be advanced, retracted, reciprocated, rotated, or a combination thereof. The cut blade can be moved beyond a distal end of the jaw assembly. The cut blade can be moved by moving or manipulating one or more of the user controls.

The cut blade may be in fluid communication with a fluid source. The cut blade may include one or more ports, channels, tubes, or passageways so that fluid can communicate from a distal end or portion of the cut blade to a proximal end or portion of the cut blade and/or the fluid source and/or a fluid pump. The cut blade, or the port or channel or passageway defined therein may be in communication with a hose or tube that extends to a fluid source. The port, channel, tube, or passageway may be located within the cut blade along its entire length, or the port, channel, tube, or passageway may be located outside of or adjacent the distal end of the cut blade or weep ports and be located within one or more of the inner and outer shafts.

In some configurations, the instrument or jaw assembly may be free of a cut blade. In such a blade-free configuration, the instrument and/or jaw assembly may be free of a jaw or blade slot that extends between the inner jaw member. Accordingly, in such a configuration, referring to FIG. 3, for example, the inner jaw member may be a single inner jaw member without a gap or slot separating the inner jaw member into two parts on opposite sides of axis 19. Likewise, with continued reference to FIG. 3, in such a blade-free configuration, the outer jaw member may also be a single outer jaw member without a gap or slot separating the outer jaw member into two parts on opposite sides of axis 19.

The instrument, the jaw assembly, the cut blade, or a combination thereof may comprise one or more weep ports. A weep port may function to provide for fluid from a fluid source to be delivered or expelled from the instrument, the jaw assembly, the cut blade, or a combination thereof. The weep port may be an opening, passage, hole, orifice, slot, port, sprayer, nozzle, or a combination thereof.

The one or more weep ports may be located on one or more sides of the cut blade. For example, relative to a longitudinal axis along which the cut blade extends, one or more of the weep ports may be located one lateral side of the axis, on both lateral sides of the axis, above the axis, below the axis, or a combination thereof.

Fluid flow from the one or more weep ports may be controlled via one or more of the user controls. For example, the fluid may be turned on and off with one or more user controls; the amount of fluid expelled from one or more weep ports may be controlled with one or more user controls; a direction of spray of the fluid from the one or more weep ports can be controlled or changed with one or more user controls; the pressure of the fluid can be controlled or changed with one or more user controls; the type of spray (e.g., mist, drip, shoot, etc.) can be changed or controlled with one or more user controls; when the fluid is expelled (i.e. during closing of the jaw assembly, while the jaw assembly is closed; while opening the jaw assembly; while the jaw assembly is open; while the cut blade is extended, retracted, rotated, during movement of the cut blade (during advancing, retracting, reciprocating, rotation, etc.); or a combination thereof.

The instrument may comprise a jaw assembly. The jaw assembly may be configured to perform one or more of the effecting functions disclosed herein. For example, the one or more effecting functions may include: capturing, gripping, clamping, and/or grasping an object or anatomical feature; providing retraction of an object or anatomical feature; providing a compression force across an object or anatomical feature captured in the jaw assembly; or a combination thereof. The jaw assembly may be used in electrosurgery to perform one or more electrically effecting functions, such as cutting, coagulating, cauterizing, dissecting, and/or fulgurating an object anatomical feature. The jaw assembly may comprise one or more jaws, one or more inner and/or outer jaw members, one or more cut blades, or a combination thereof.

The jaw assembly may include one or more jaws. One or more of the jaws may be configured to perform one or more of the effecting functions disclosed herein.

The jaw assembly may comprise two jaws. The two jaws may be arranged to oppose one another. The jaws may include an upper jaw and an opposing lower jaw; a first jaw and an opposing second jaw; or a combination thereof. One or both of the jaws may comprise an outer jaw member and/or an inner jaw member. That is, both of the first and second jaws may comprise both an outer jaw member and an inner jaw member. Or alternatively, one of the jaws may comprise an outer jaw member and an inner jaw member, while the other one of the jaws comprises only an outer jaw member o only an inner jaw member.

One or both of the first and second jaws may comprise an outer jaw member. An outer jaw member may be a jaw member that is located at least partially distal of a distal most end of one or both of the inner jaw members (i.e., first and/or second inner jaw members). An outer jaw member may be a jaw or jaw member that is located farther away from a hand piece than one or both of the inner jaw members. An outer jaw member may be a jaw or jaw member that is located laterally farther away from a center or longitudinal axis of the jaw assembly. An outer jaw member may be a jaw or jaw member that is located proud of an inner jaw member. Proud means that the outer jaw member may be located closer to an opposing jaw than the corresponding inner jaw member. Proud means that a gap defined between a portion of the outer jaw member and the opposing jaw is smaller than a gap defined between the corresponding inner jaw member and the opposing jaw.

The outer jaw member may function to effect an object or anatomical feature. The outer jaw member may function to effect an object or anatomical feature when the jaw assembly is in the open configuration, the closed configuration, the first closed configuration, the second closed configuration, or a combination thereof. The outer jaw member may function to effect a portion of an object or anatomical feature that is laterally spaced away from the center longitudinal axis, the inner jaw members, or both. The outer jaw member may function to effect a portion of an object or anatomical feature that is distally spaced away from the inner jaw member. The outer jaw members may function to effect a portion of an object or anatomical feature before the inner jaw members are configured to effect a portion of the object or anatomical feature. The outer jaw members may function to effect a portion of an object or anatomical feature while the opposing inner jaw members are spaced apart from one another or are not configured to effect a portion of the object or anatomical feature.

The outer jaw member may be connected to the inner jaw member. An outer jaw member may be connected to the corresponding inner jaw member by an element that allows or provides for the inner jaw member to move relative to the outer jaw member. The inner jaw member may move away from the outer jaw member that it is connected to when the jaw assembly is moved from the first closed configuration to the second closed configuration. The inner jaw member may move towards the outer jaw member that it is connected to when the jaw assembly is moved from the second closed configuration to the first closed configuration, or from the second closed configuration to the open configuration.

The instrument, the jaw assembly, or both may comprise one or more elements for connecting the outer jaw member to the inner jaw member.

The one or more elements may function to maintain a position or relative location of the corresponding inner and outer jaw members while the jaw assembly is in an open configuration or in one or more of the closed configurations. The one or more elements may function to allow the inner jaw member to move relative to the outer jaw member, or vice versa, when a pressing force is applied onto the inner jaw member via the outer shaft or a with a user's fingers in the case the instrument is tweezers.

The one or more elements may function to allow the inner jaw member to move away from the outer jaw member so that a gap defined between the inner and outer jaw members increases when a force is applied onto the inner shaft. After the force is reduced or removed from the inner jaw member, the one or more elements may function to move or pull the inner jaw member towards the outer jaw member. After the force is reduced or removed from the inner jaw member, the one or more elements may function to draw the inner jaw member towards the outer jaw member so that a gap defined between the corresponding inner and outer jaw member decreases. The inner jaw members may move away from the outer jaw members during movement of the jaw assembly into the second closed configuration and thus the corresponding elements may stretch or expand during movement of the jaw assembly into the second closed configuration and/or while the jaw assembly is in the second closed configuration. The inner jaw members may move towards the outer jaw members and/or be maintained adjacent the outer jaw members (i.e., elements not stretched or expanded) during movement of the jaw assembly into the open configuration and/or the first closed configuration and/or while the jaw assembly is in the open configuration and/or first closed configuration.

The one or more elements may be a biasing member, a spring, a coil spring, an extension spring, or a combination thereof. The one or more elements may be an elastic, compressible, resilient, bias able, elastomeric, or a combination thereof.

One or more elements may be located between the first inner jaw member and the corresponding first outer jaw member, and one or more elements may be located between the second inner jaw member and the corresponding second outer jaw member.

The one or more elements may be an insulator to prevent the inner jaw members and the outer jaw members from directly contacting each other and causes an electrical short.

The one or more elements may be insulators to insulate, restrict, and/or prevent the corresponding inner and outer jaw members from directly contacting each other to prevent the instrument from arcing or shorting during electrosurgical procedures. The one or more elements or insulators may be formed from any suitable material having insulating properties such as, for example, Nylon, PEEK, silicon rubber, a ceramic material, or a combination thereof.

One or both of the first and second jaws may comprise an inner jaw member. The inner jaw member may be connected to the outer jaw member. The inner jaw member may be connected to the outer shaft, the inner shaft, or both via one or more pivot joints. The inner jaw member may function to effect an object or anatomical feature. The inner jaw member may function to effect an object or anatomical feature when the jaw assembly is in the open configuration, the closed configuration, the first closed configuration, the second closed configuration, or a combination thereof. The inner jaw members may function to effect a portion of an object or anatomical feature after the outer jaw members have effected a portion of the object or anatomical feature. The inner jaw members may function to effect a portion of an object or anatomical feature while the opposing outer jaw members are effecting a portion of the object or anatomical feature.

The jaw assembly, the first jaw, the second jaw, the outer jaw members, the inner jaw members, or a combination thereof may comprise an effecting surface. An effecting surface may function to contact or grip an object or anatomical feature. An effecting surface may function to effect an object or anatomical feature.

An effecting surface may be generally smooth. This means that an effecting surface may be free of teeth or texture. Alternatively, an effecting surface may have a texture or teeth to aid in gripping, pulling, or clamping of an object or anatomical feature. An effecting surface may have portions that are generally smooth and portions that are textured or have teeth.

One effecting surfaces may be in electrical communication with a pole of the power source so that an object or anatomical feature can be electrically effected with one or more effecting surfaces.

An effecting surface may comprise one or more standoffs or insulators. The one or more standoffs or insulators may function to insulate, restrict, and/or prevent opposing jaws and/or opposing sealing surfaces from directly contacting each other to prevent the instrument from arcing or shorting during electrosurgical procedures. The one or more standoffs or insulators may be formed from any suitable material having insulating properties such as, for example, Nylon, PEEK, silicon rubber, a ceramic material, or a combination thereof. The one or more standoffs or insulators may be located on only one sealing surface, jaw, jaw member, or on both opposing jaws, sealing surfaces, inner jaw members, outer jaw members or a combination thereof.

The instrument, the jaw assembly, or both may comprise one or more pivot joints. A pivot joint may function to allow a jaw, an outer jaw member, or both to move, pivot, and/or rotate. A pivot joint may be used to connect an inner jaw member to the outer shaft, an inner jaw member to the inner shaft, or both.

A pivot joint may function to allow the jaw assembly to move into an open configuration, into a closed configuration, the first closed configuration, the second closed configuration, or a combination thereof.

For example, when the outer shaft is moved distally in a direction away from the hand piece, one or both of the inner jaw members may pivot about a pivot joint connecting the inner jaw members and the inner shaft, a pivot joint connecting the inner jaw members and the outer shaft, or both so that the opposing jaws, are closed or moved towards each other. For example, when the outer shaft is moved proximally in a direction towards the hand piece, one or both of the inner jaw members may pivot about a pivot joint connecting the inner jaw members and the inner shaft, a pivot joint connecting the inner jaw members and the outer shaft, or both so that the opposing jaws are opened or moved away from each other.

A pivot joint may comprise a pin or axle and one or more corresponding slots or openings. The slots or openings may be configured to receive a pin or axle to create a pivot joint. The openings may be defined in the inner shaft, the outer shaft, the inner jaw member, or a combination thereof.

The instrument or the jaw assembly may be moved into one or more configurations. The configurations may include an open configuration and a closed configuration. The closed configuration may comprise a first closed configuration and a second closed configuration.

The jaw assembly may be moved or sequentially moved from the open configuration into the closed configuration. The jaw assembly may be configured to move or sequentially moved from the open configuration into the first closed configuration. The jaw assembly may be configured to move or sequentially moved from the first closed configuration into the second closed configuration. The jaw assembly may be configured to move or sequentially moved from the open configuration into the second closed configuration. The jaw assembly may be configured to move or sequentially moved from the second configuration into the first closed configuration. The jaw assembly may be configured to move or sequentially moved from the first closed configuration into the open configuration. The jaw assembly may be configured to move or sequentially move from the second configuration in the open configuration.

The open configuration may be a steady state position of the jaws. The jaw assembly may be moved from the open configuration to the closed configuration by manipulating one or more user controls. In some configurations, the closed configuration (the first or the second closed configuration) may be a steady state position, and the jaw assembly may be moved from the closed configuration to the open configuration by manipulating one or more user controls.

When moving into the closed configuration or into the first closed configuration, one jaw may move towards the other jaw, or both jaws may move towards each other. That is, one jaw may move towards the other jaw by rotating or pivoting about one or more pivot joints, or both jaws may move towards each other by rotating about one or more pivot joints. One or both jaws may rotate or pivot by moving the outer shaft relative to the stationary inner shaft along direction of the longitudinal axis. One or both jaws may rotate or pivot by moving the inner shaft relative to the stationary outer shaft along direction of the longitudinal axis. In some configurations, the jaw or jaws may rotate or pivot about a living hinge or flexing point by applying a force onto the corresponding jaw or jaws with the outer shaft or with finger pressure (i.e., in the case of tweezers).

The open configuration may be defined as a position of the jaws or jaw members where the jaws or jaw members are spaced apart from each other. For example, in the open configuration, a gap may be defined between the opposing jaws, between the opposing effecting surfaces of the first and second outer jaw members, between the opposing effecting surfaces of the first and second inner jaw members, or a combination thereof. In the open configuration, a clamping or gripping force of the effecting surfaces is lower or less than a clamping or gripping force between the effecting surfaces when the jaws are in the closed configuration.

In the open configuration, the effecting surfaces of the outer jaw members may be proud of the effecting surfaces of the inner jaw members. This means that in the open configuration, the effecting surfaces of the first outer jaw member are lower or closer to the effecting surfaces of the second jaw than the effecting surfaces of the first inner jaw member.

The closed configuration may be defined as a position of the jaws or jaw members where a gap may between the opposing jaws, between the opposing effecting surfaces of the first and second outer jaw members, between the opposing effecting surfaces of the first and second inner jaw members, or a combination thereof is less than when the jaw assembly is in the open configuration. In the closed configuration, a clamping or gripping force of the effecting surfaces is higher or greater than a clamping or gripping force between the effecting surfaces when the jaws are in the open configuration.

The first closed configuration may be defined as a position of the jaws or jaw members where a gap may exist between the opposing jaws, between the opposing effecting surfaces of the first and second outer jaw members, between the opposing effecting surfaces of the first and second inner jaw members, or a combination thereof is less than the gap when the jaw assembly is in the open configuration. The first closed configuration may be defined as a position of the jaws or jaw members where virtually no gap, or only a slight gap exists between the opposing jaws, between the opposing effecting surfaces of the first and second outer jaw members, between the opposing effecting surfaces of the first and second inner jaw members, or a combination thereof. When an object or anatomical feature is located between the jaws, the effecting surfaces of the first and second outer jaw members may be configured to apply a gripping or clamping force onto the object or anatomical feature.

In the first closed configuration, the opposing sealing surfaces of the outer jaw members may be in contact or close proximity thereto and apply a gripping or clamping force on an object or anatomical feature located therebetween. In the first closed configuration, the opposing sealing surfaces of the inner jaw members may be spaced apart and apply no gripping or clamping force on an object or anatomical feature located therebetween, or low gripping or clamping force on the object or anatomical feature.

In the first closed configuration, the effecting surfaces of the outer jaw members may be proud of the effecting surfaces of the inner jaw members. This means that in the first closed configuration the effecting surfaces of the first outer jaw member are lower or closer to the effecting surfaces of the second jaw than the effecting surfaces of the first inner jaw member.

The second closed configuration may be defined as a position of the jaws or jaw members where a gap between the opposing jaws, between the opposing effecting surfaces of the first and second outer jaw members, between the opposing effecting surfaces of the first and second inner jaw members, or a combination thereof is less than when the jaw assembly is in the open configuration. In the second closed configuration, the opposing sealing surfaces of the outer jaw members may be in contact or close proximity thereto and apply a gripping or clamping force on an object or anatomical feature located therebetween. In the second closed configuration, the opposing sealing surfaces of the inner jaw members may be in contact or close proximity thereto and apply a gripping or clamping force on an object or anatomical feature located therebetween.

In the second closed configuration, the effecting surfaces of the outer jaw members may be on the same plane of the effecting surfaces of the inner jaw members. This means that in the open configuration, a position of the effecting surfaces of the first outer jaw member are generally the same as a position of the effecting surfaces of the first inner jaw member relative to the effecting surfaces of the second jaw.

FIG. 1 illustrates the medical instrument 10. The medical instrument 10 comprises a hand piece 12. The medical instrument 10 comprises an outer shaft 14 extending from the hand piece 12. The medical instrument 10 comprises an inner shaft 16 extending from the hand piece 12. The inner shaft 16 is located within the outer shaft 14. The outer and inner shafts 14, 16 extend along a longitudinal axis 18.

The hand piece 12 comprises one or more user controls that may include: a lever 22, a trigger 24, a wheel 26, and a button 28. The medical instrument 10 may be in electrical communication with a power source 30. The medical instrument 10 may be in fluid communication with a fluid source 32. The medical instrument 10 comprises a jaw assembly 100. The jaw assembly comprises a first jaw 102 and an opposing second jaw 104.

Figure 2:
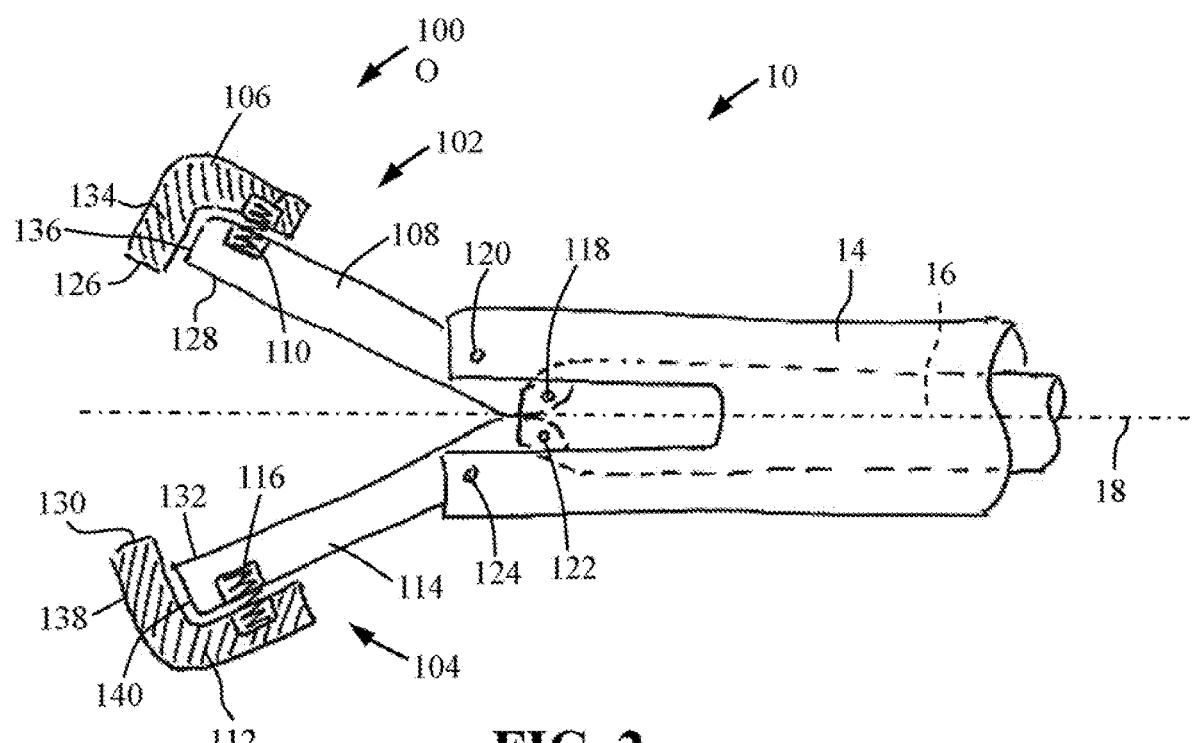
FIG. 2 is cross-sectional view of a jaw assembly in an open configuration.

FIG. 2 illustrates a distal portion of the medical instrument 10 of FIG. 1, with the jaw assembly 100 in the open configuration O. The jaw assembly comprises a first jaw 102 and a second jaw 104.

The first jaw 102 comprises a first outer jaw member 106 comprising an effecting surface 126; a first inner jaw member 108 comprising an effecting surface 128; and an element 110 connecting the first outer jaw member 106 and the first inner jaw member 108. Relative to the hand piece 12 (FIG. 1), the effecting surface 126 of the first outer jaw member 106 is located distal of the effecting surface 128 of the first inner jaw member 108. Relative to the hand piece 12 (FIG. 1), the distal-most end 134 of the first outer jaw member 106 is located distal of a distal-most end 136 of the first inner jaw member 108.

The element 110 connecting the first outer jaw member 106 and the first inner jaw member 108 may be configured to provide for or allow the first inner jaw member 108 to move relative to the first outer jaw member 106. This means that the element 110 provides for, allows, or is configured to allow the first inner jaw member 108 to move or translate towards and away from the second jaw 104, second inner jaw member 114, the longitudinal axis 18, or a combination thereof, while the first outer jaw member 106 does not move or generally stays in the same position. Movement of the first inner jaw member 108 relative to the first outer jaw member 106 may occur during movement of the jaw assembly 100 into the second closed configuration discussed further below.

A proximal end of the first inner jaw member 108 is connected to the inner shaft 16 at a pivot joint 118. A proximal portion of the first inner jaw member 108, which is located distal of the proximal end of the first inner jaw member 108, is connected to a distal end of the outer shaft 14 at a pivot joint 120. Pivot joint 120 is located distal of pivot joint 118. Pivot joint 120 may be located farther away from the longitudinal axis 18 than pivot joint 118. That is, a gap defined between the pivot joint 120 and the longitudinal axis 18 is greater than or larger than a gap defined between the pivot joint 118 and the longitudinal 18.

The second jaw 104 comprises a second outer jaw member 112 comprising an effecting surface 130; a second inner jaw member 114 comprising an effecting surface 132; and an element 116 connecting the second outer jaw member 112 and the second inner jaw member 114. Relative to the hand piece 12 (FIG. 1), the effecting surface 130 of the second outer jaw member 112 is located distal of the effecting surface 132 of the second inner jaw member 114. Relative to the hand piece 12 (FIG. 1), a distal-most end 138 of the second outer jaw member 112 is located distal of a distal-most end 140 of the second inner jaw member 114.

The element 116 connecting the second outer jaw member 112 and the second inner jaw member 114 may be configured to provide or allow for the second inner jaw member 114 to move relative to the second outer jaw member 112. This means that the element 116 provides, allows, or is configured to allow the second inner jaw member 114 to move or translate towards and away from the first jaw 102, the first inner jaw member 108, the axis 18, or a combination thereof, while the second outer jaw member 112 does not move or stays generally in the same position. Movement of the second inner jaw member 114 relative to the second outer jaw member 112 may occur during movement of the jaw assembly 100 into the second closed configuration discussed further below.

A proximal end of the second inner jaw member 114 is connected to the inner shaft 16 at a pivot joint 122. A proximal portion of the second inner jaw member 114, which is located distal of the proximal end of the second inner jaw member 114, is connected to a distal end of the outer shaft 14 at a pivot joint 124. Pivot joint 124 is located distal of pivot joint 122. Pivot joint 124 may be located farther from the axis 18 than pivot joint 122. That is, a gap defined between pivot joint 124 and axis 18 is greater than or larger than a gap defined between pivot joint 122 and axis 18.

Pivot joint 124 and pivot joint 120 may be arranged along a common axis or plane that is generally perpendicular to the longitudinal axis 18. Pivot joint 122 and pivot joint 118 may also be arranged along a common axis of plane that is generally perpendicular to the longitudinal axis 18.

In some configurations, pivot joint 122 and pivot joint 118 may be combined at a single pivot joint that is configured to connect the proximal ends of the first and second inner jaw members 108, 114 to a distal end of the inner shaft 16. That is, a single pin may extend through respective bores defined in the first and second inner jaw members 108, 114 and a single bore defined at a distal end of the inner shaft 16.

To move the jaw assembly 100 from the open configuration O illustrated in FIG. 2 into a first closed configuration, the outer shaft 14 may be moved in a distal direction away from the hand piece 12 (FIG. 1). The inner shaft 16 is axially fixed to the hand piece 12 and therefore does not move relative to the hand piece 12 and/or outer shaft 14. Distal movement of the outer shaft 14 functions to apply a pressing force onto one or both of the inner jaw members 108, 114, which causes one or both of the inner jaw members 108, 114 to move or pivot about the corresponding pivot joints 120, 118 and/or 124, 122 towards the longitudinal axis 18 and/or towards each other.

One or both of the inner jaw members 108, 114 may pivot towards each other and/or towards the longitudinal axis 20 until the opposing effecting surfaces 126, 130 of the outer jaw members 106, 112 contact each other or contact opposing sides of an object or anatomical feature (not illustrated) located between the jaws 102, 104 and apply a clamping force or otherwise effect the object or anatomical feature. For example, in the first closed configuration, the opposing effecting surfaces 126, 130 of the outer jaw members 106, 112 may pinch or clamp the anatomical feature to stop blood flow through the anatomical feature. During the first closed configuration, the opposing effecting surfaces 128, 132 of the inner jaw members 108, 114 may be spaced apart from each other or from the object or anatomical feature and free from contacting the object of anatomical feature (i.e., a gap is defined between the effecting surfaces 128, 132 and the object or anatomical feature).

Alternatively, in the first closed configuration, the opposing effecting surfaces 128, 132 may be in contact with the object or anatomical feature but apply a lower clamping force onto the object or anatomical feature compared to the clamping force that is applied onto the object or anatomical feature by the effecting surfaces 126, 130 of the outer jaw members 106, 112.

In an operation during movement of the jaw assembly 100 into the first closed configuration, or in an operation after the jaw assembly has been moved in the first closed configuration, the object or anatomical feature can be cut or effected with a cut blade (e.g., cut blade 200 at FIG. 5); a fluid can be directed or sprayed onto the anatomical feature (e.g., fluid F at FIG. 5); and/or a therapy current can be applied onto the anatomical feature from one or more portions of the jaw assembly 100 that are in electrical communication with the power source (e.g., power source 30 at FIG. 1).

To move the jaw assembly 100 from the first closed configuration into the second closed configuration, the outer shaft 14 can be moved further in a distal direction away from the hand piece 12 (FIG. 1). Further distal movement of the outer shaft 14 functions to apply additional pressing force onto one or both of the inner jaw members 108, 114. However, because the outer jaw members 106, 112 are already in contact with each other or in contact with the object or anatomical feature (i.e., the outer jaw members 106, 112 are in the first closed configuration), the additional pressing force applied onto one or both of the inner jaw members 108, 114 functions to cause one or both of the opposing inner jaw members 108, 114 to move towards each other and/or towards the center axis 20. In other words, one or both of the elements 110, 116 expand or stretch, which therefore causes or allows one or both of the inner jaw member 108, 114 to move away from the respective outer jaw member 106, 112 and closer towards the longitudinal axis 20 and/or each other so that the effecting surfaces 128, 132 contact each other or contact the anatomical feature, and/or apply a greater gripping force onto the anatomical feature than the clamping force applied by the effecting surface 128, 132 when the jaw assembly 100 is in the first closed configuration.

In an operation during movement of the jaw assembly 100 into the second closed configuration, or in an operation after the jaw assembly has been moved in the second closed configuration, the anatomical feature can be cut or effected with a cut blade (e.g., cut blade 200, FIG. 5); a fluid can be provided onto the anatomical feature (e.g., fluid F at FIG. 5); and/or a therapy current can be applied onto the anatomical feature from one or more portions of the jaw assembly that are in electrical communication with the power source (e.g., power source 30 at FIG. 1).

By moving the outer shaft 14 proximally towards the hand piece, the pressing force applied onto one or both of the inner jaw members 108, 114 is reduced or eliminated, which allows or causes the jaws 102, 104 to move or pivot about the respective pivot joints 120, 118 and 124, 122 so that the jaw assembly 100 is moved from the second closed configuration into either the first closed configuration or into the open configuration O illustrated in FIG. 2.

Of course, moving the outer shaft 14 proximally towards the hand piece while the jaw assembly 100 is in the first closed configuration may function to move the jaw assembly 100 into the open configuration illustrated in FIG. 2.

One or more of: the first outer jaw member 106, the second outer jaw member 112, the first inner jaw member 108, the second inner jaw member 114, the effecting surface 126, the effecting surface 128, the effecting surface 130, the effecting surface 132, a cut blade 200 (FIG. 5) or a combination thereof may be in electrical communication with a pole of the power source 30 (FIG. 1). This means that one or more of the aforementioned elements 106, 112, 108 114, 126, 128, 130, 132, 200 may cooperate to electrically effect an object or anatomical feature during a procedure when the jaw assembly 100 is in an open configuration O and/or in one or both of the closed configurations.

For example, the first and second outer jaw members 106, 112 and/or the corresponding effecting surfaces 126, 130 may be in electrical communication with opposing poles of the power source 30 so that during a procedure an object or anatomical feature between the jaws 102, 104 can be electrically effected with one or more bipolar therapy signals passed between the poles when the jaw assembly 100 is in an open configuration O and/or one or both of the closed configurations.

For example, the first and second inner jaw members 108, 114 and/or the corresponding effecting surfaces 128, 132 may be in electrical communication with opposing poles of the power source 30 so that during a procedure an object or anatomical feature between the jaws 102, 104 can be electrically effected with one or more bipolar therapy signals passed between the poles of the power source 30 when the jaw assembly 100 is in an open configuration O and/or one or both of the closed configurations.

One or more of the aforementioned elements 106, 112, 126, 130, 108, 114, 128, 132, 200 may be in electrical communication with a single pole of the power source 30, and a remote electrode can be in electrical communication with an opposing pole of the power source 30 so that an object or anatomical feature can be electrically effected with one or more monopolar therapy signals passed between the poles of the power source 30 when the jaw assembly 100 is in an open configuration O and/or in one or both of the closed configurations.

Figure 3:
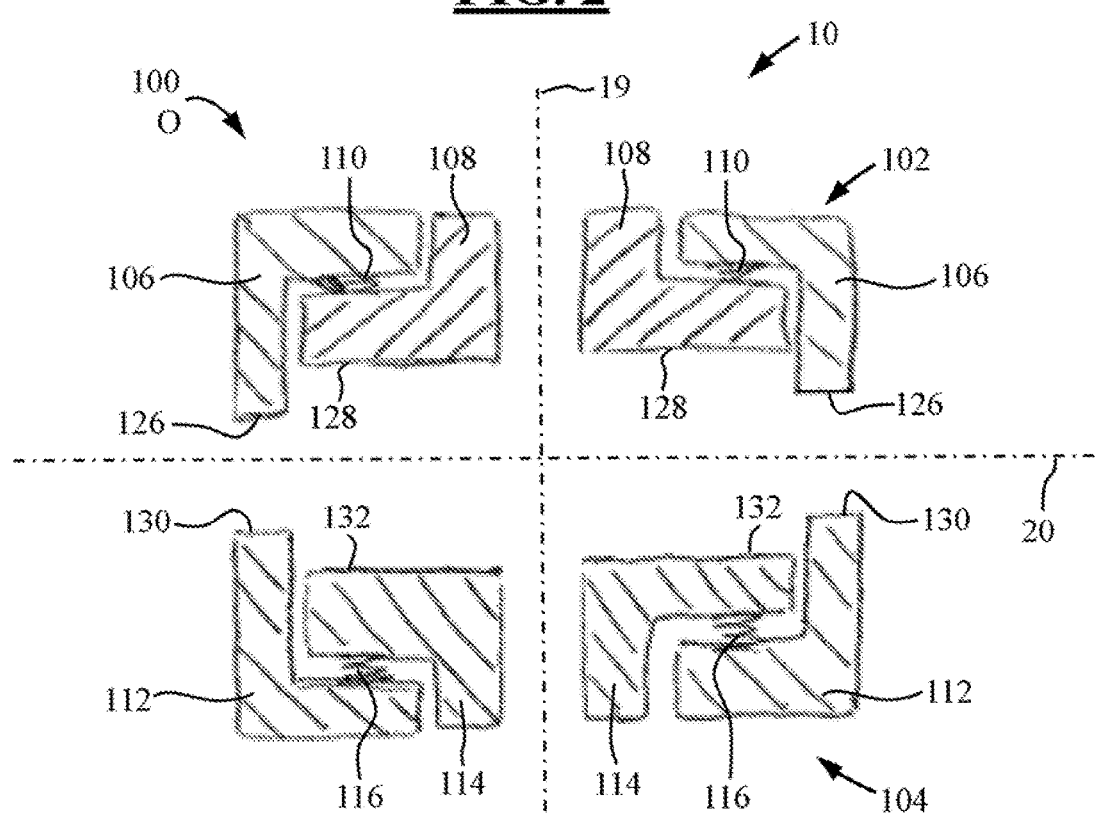
FIG. 3 is cross-sectional view of another jaw assembly in an open configuration.

FIG. 3 illustrates a distal portion of the medical instrument 10, with the jaw assembly 100 in the open configuration O. The jaw assembly comprises a first jaw 102 and a second jaw 104.

The first jaw 102 comprises a first outer jaw member 106 comprising an effecting surface 126; a first inner jaw member 108 comprising an effecting surface 128; and an element 110 connecting the first outer jaw member 106 and the first inner jaw member 108. The first inner jaw member 108 may be connected to the inner and outer shafts 16, 14 via pivot joints, like those illustrated in FIG. 2 (See pivot joints 118, 120).

The first outer jaw member 106 and/or the effecting surface 126 of the first outer jaw member 106 is laterally proud of the first inner jaw member 108 and/or the effecting surface 128 of the first inner jaw member 108. Laterally proud means that the first outer jaw member 106 and/or the effecting surface 126 of the first outer jaw member 106 is laterally offset farther away from a center or longitudinal axis or plane 19 compared to the first inner jaw member 108 and/or the effecting surface 128 of the first inner jaw member 108. The center or longitudinal axis or plane 19 may extend generally perpendicular to the longitudinal axis 18, which is the axis that the outer and inner shafts 14, 16 extend along in FIGS. 1 and 2.

In the jaw assembly 100 open configuration O illustrated in FIG. 3, the effecting surface 126 of the first outer jaw member 106 is proud of the effecting surface 128 of the first inner jaw member 108 in a direction of the second jaw 104. Proud means that the effecting surface 126 of the first outer jaw member 106 is located or arranged closer to the second jaw 104 and/or to an axis or plane 20 than the effecting surface 128 of the first inner jaw member 108. Proud means that a gap defined between the effecting surface 126 of the first outer jaw member 106 and the second jaw 104 and/or the axis or plane 20 is smaller or less than a gap defined between the effecting surface 128 of the first inner jaw member 108 and the second jaw 104 and/or the axis or plane 20. The center axis or plane 20 may extend generally perpendicular to center axis or plane 19 and/or longitudinal axis 18 in FIGS. 1 and 2. Proud means that a gap defined between the effecting surface 126 of the first outer jaw member 106 and an effecting surface 130 of a second outer jaw member 112 is smaller or less than a gap defined between the effecting surface 128 of the first inner jaw member 108 and an effecting surface 132 of a second inner jaw member 114.

The element 110 connecting the first outer jaw member 106 and the first inner jaw member 108 may be configured to provide or allow for the first inner jaw member 108 to move relative to the first outer jaw member 106. This means that the element 110 provides, allows, or is configured to allow the first inner jaw member 108 to move or translate towards and away from the second jaw 104, second inner jaw member 114, the axis 18, or a combination thereof, while the first outer jaw member 106 does not move or stays in generally the same place. Movement of the first inner jaw member 108 relative to the first outer jaw member 106 may occur during movement of the jaw assembly 100 into the second closed configuration C2, illustrated at FIG. 6.

The second jaw 104 comprises a second outer jaw member 112 comprising an effecting surface 130; a second inner jaw member 114 comprising an effecting surface 132; and an element 116 connecting the second outer jaw member 112 and the second inner jaw member 114. The second inner jaw member 114 may be connected to the inner and outer shafts 16, 14 via pivot joints, like those illustrated in FIG. 2 (See pivot joints 122, 124).

The second outer jaw member 112 and/or the effecting surface 130 of the second outer jaw member 112 is laterally proud of the second inner jaw member 114 and/or the effecting surface 132 of the second inner jaw member 114. Laterally proud means that the second outer jaw member 112 and/or the effecting surface 130 of the second outer jaw member 112 is laterally offset farther from a center or longitudinal axis or plane 19 compared to the second inner jaw member 114 and/or the effecting surface 132 of the second inner jaw member 114.

In the open configuration O, the effecting surface 130 of the second outer jaw member 112 is proud of the effecting surface 132 of the second inner jaw member 114 in a direction of the first jaw 102. Proud means that the effecting surface 130 of the second outer jaw member 112 is located or arranged closer to the first jaw 102 and/or to the axis or plane 20 than the effecting surface 132 of the second inner jaw member 114. Proud means that a gap defined between the effecting surface 130 of the second outer jaw member 112 and the first jaw 102 and/or the axis or plane 20 is smaller or less than a gap defined between the effecting surface 132 of the second inner jaw member 114 and the first jaw 102 and/or axis or plane 20. Proud means that a gap defined between the effecting surface 130 of the second outer jaw member 112 and the effecting surface 126 of the first outer jaw member 106 is smaller or less than a gap defined between the effecting surface 132 of the second inner jaw member 114 and the effecting surface 128 of the first inner jaw member 108.

The element 116 connecting the second outer jaw member 112 and the second inner jaw member 114 may be configured to provide or allow for the second inner jaw member 114 to move relative to the second outer jaw member 112. This means that the element 116 provides, allows, or is configured to allow for the second inner jaw member 114 to move or translate towards and away from the first jaw 102, the first inner jaw member 108, the axis 18, or a combination thereof, while the second outer jaw member 112 does not move or stays in generally the same place. Movement of the second inner jaw member 114 relative to the second outer jaw member 112 may occur during movement of the jaw assembly 100 into the second closed configuration C2, illustrated at FIG. 6.

One or more of: the first outer jaw member 106, the second outer jaw member 112, the first inner jaw member 108, the second inner jaw member 114, the effecting surface 126, the effecting surface 128, the effecting surface 130, the effecting surface 132, a cut blade 200 (FIG. 5) or a combination thereof may be in electrical communication with a pole of the power source 30 (FIG. 1). This means that one or more of the aforementioned elements 106, 112, 108 114, 126, 128, 130, 132, 200 may cooperate to electrically effect an object or anatomical feature during a procedure when the jaw assembly 100 is in an open configuration O or one or both of the closed configurations.

For example, the first and second outer jaw members 106, 112 and/or the corresponding effecting surfaces 126, 130 may be in electrical communication with opposing poles of the power source 30 so that during a procedure an object or anatomical feature between the jaws 102, 104 can be electrically effected with one or more bipolar therapy signals passed between the poles when the jaw assembly 100 is in an open configuration O or one or both of the closed configurations.

For example, the first and second inner jaw members 108, 114 and/or the corresponding effecting surfaces 128, 132 may be in electrical communication with opposing poles of the power source 30 so that during a procedure an object or anatomical feature between the jaws 102, 104 can be electrically effected with one or more bipolar therapy signals passed between the poles of the power source 30 when the jaw assembly 100 is in an open configuration O or one or both of the closed configurations.

One or more of the aforementioned elements 106, 112, 126, 130, 108, 114, 128, 132 can be in electrical communication with a single pole of the power source 30, and a remote electrode can be in electrical communication with an opposing pole of the power source 30 so that an object or anatomical feature can be electrically effected with one or more monopolar therapy signals passed between the poles of the power source 30 when the jaw assembly 100 is in an open configuration O or one or both of the closed configurations.

It is understood that an embodiment of the instrument 100 may exist that includes features of the jaw assembly 100 from both FIGS. 2 and 3. That is, for example, such a jaw assembly 100 may comprise opposing jaws 102, 104 that each comprise one or both inner jaw members 108, 114 and one or both outer jaw members 106, 112 connected via elements 110, 116. One or both of the effecting surfaces 126, 130 of outer jaw members 106, 112 may be located distal of one or both of the effecting surfaces 128, 132 of the inner jaw members 108, 114 (See FIG. 2), and one or both of the effecting surfaces 126, 130 of outer jaw members 106, 112 may also be proud of one or both of the effecting surfaces 128, 132 of the inner jaw members 108, 114 (FIG. 3). Such a configuration may also optionally include a cut blade 200.

Figure 4:
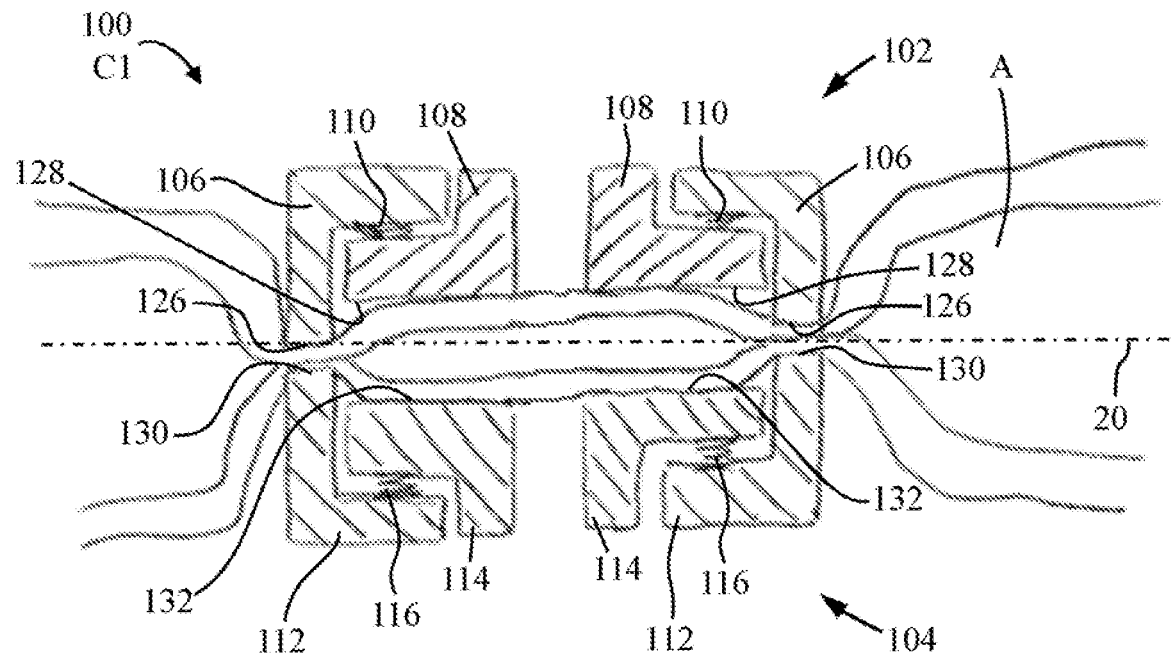
FIG. 4 is cross-sectional view of the jaw assembly of FIG. 3 in a first closed configuration.

FIG. 4 illustrates the jaw assembly 100 of FIG. 3 in a closed configuration, which may also be referred to as the first closed configuration C1. To move the jaw assembly 100 from the open configuration O illustrated in FIG. 3 into the first closed configuration C1, the outer shaft 14 (FIG. 1) may be moved in a distal direction away from the hand piece 12 (FIG. 1). The inner shaft 16 is axially fixed to the hand piece 12 and therefore does not move relative to the hand piece 12. Distal movement of the outer shaft 14 functions to apply a pressing force onto one or both of the inner jaw members 108, 114, which functions to cause one or both of the inner jaw members 108, 114 to move or pivot about the corresponding pivot joints 120, 118, 124, 122 (FIG. 2) towards the longitudinal axis 18 and/or towards each other. One or both of the inner jaw members 108, 114 pivot towards each other and/or towards the center axis 20 until the opposing effecting surfaces 126, 130 of the outer jaw members 106, 112 contact opposing sides of an object or anatomical feature A located between the jaws 102, 104 and apply a clamping force or otherwise effect the object or anatomical feature A.

For example, in the first closed configuration, the effecting surfaces 126, 130 of the opposing outer jaw members 106, 112 may pinch or clamp the anatomical feature A to stop blood flow through the anatomical feature A. During the first closed configuration, the effecting surfaces 128, 132 of the inner jaw members 108, 114 may be spaced apart from the anatomical feature A. That is, a gap may be defined between the anatomical feature and one or both of the effecting surfaces 128, 132. Alternatively, the effecting surfaces 128, 132 may be configured to contact the anatomical feature A but apply a lower clamping force onto the anatomical feature A compared to the clamping force that is applied onto the anatomical feature A by the effecting surfaces 126, 130 of the outer jaw members 106, 112.

Similar to the open configuration O discussed above at FIG. 3, the effecting surface 126 of the first outer jaw member 106 is proud of the effecting surface 128 of the first inner jaw member when the jaw assembly is in the first closed configuration C1. Also, in the first closed configuration C1, the effecting surface 130 of the second outer jaw member 112 is proud of the effecting surface 132 of the second inner jaw member 114.

Figure 5:
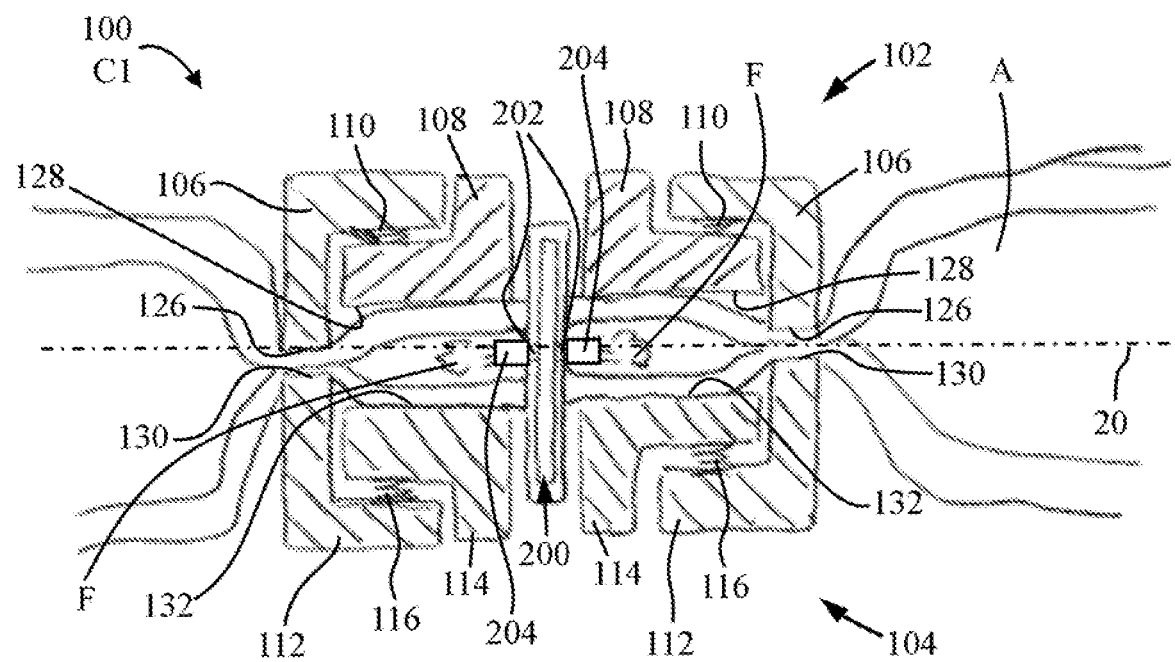
FIG. 5 is cross-sectional view of the jaw assembly of FIG. 3 in the first closed configuration.

FIG. 5 illustrates the jaw assembly 100 in a closed configuration, which may also be referred to as the first closed configuration C1. The jaw assembly 100 comprises a cut blade 200. A distal end of the cut blade 200 may be configured to cut or otherwise effect the anatomical feature A. The cut blade 200 comprises one or more weep ports 204. The weep ports 204 may be configured to deliver or expel a fluid F to or toward the anatomical feature A before, during, or after the anatomical feature A is effected with the jaw assembly 100 or cut blade 200 in either the open configuration O, the first closed configuration C1, or the second closed configuration C2. In FIG. 5, the fluid F is delivered or applied onto the anatomical feature after the jaw assembly 100 is in the first closed configuration and the cut blade 200 has cut the anatomical feature A.

The cut blade 200 may be in electrical communication with a pole of the power source, and one or more of the first outer jaw member 106, the second outer jaw member 112, the first inner jaw member 108, the second inner jaw member 114, the effecting surface 126, the effecting surface 128, the effecting surface 130, the effecting surface 132 may be in electrical communication with an opposing pole of the power source 30 so that an object or anatomical feature A can be electrically effected with one or more bipolar therapy signals passed between the poles of the power source 30. The cut blade 200 may be in electrical communication with a pole of the power source, and an opposing pole of the power source can be in electrical communication with a remote electrode so that an object or anatomical can be electrically effected with one or more monopolar therapy signals passed between the poles of the power source 30 when the jaw assembly 100 is in an open configuration O or one or both of the closed configurations.

Figure 6:
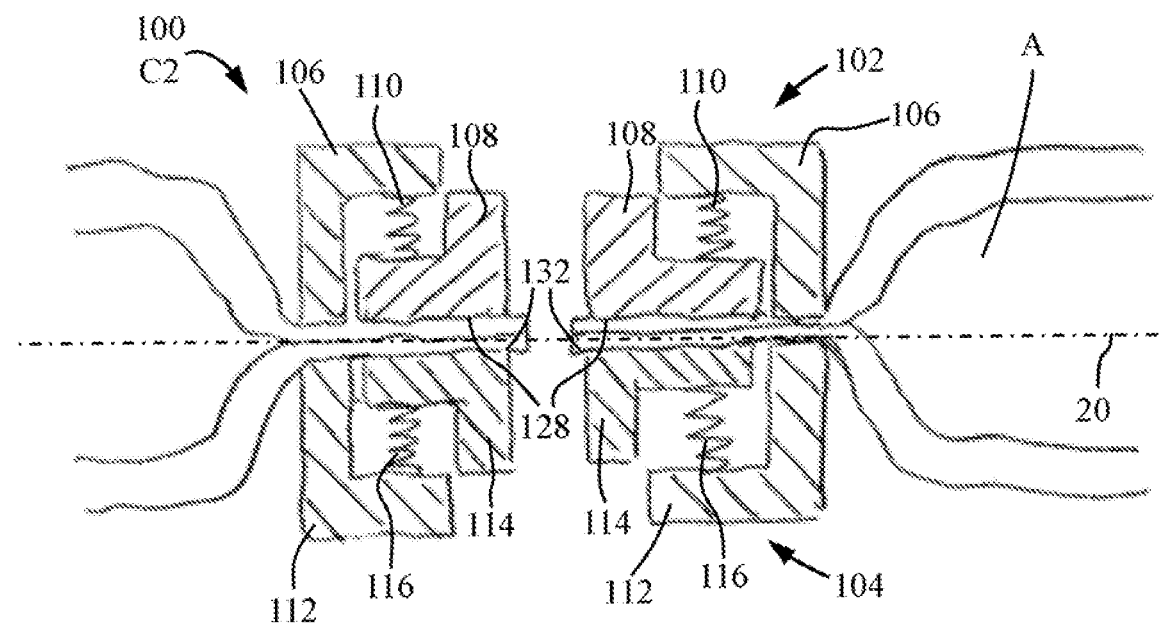
FIG. 6 is cross-sectional view of the jaw assembly of FIG. 3 in a second closed configuration.

FIG. 6 illustrates the jaw assembly 100 in a closed configuration, which may also be referred to as the second closed configuration C2.

To move the jaw assembly 100 from the first closed configuration C1 in FIG. 4 or 5 to the second closed configuration C2, the outer shaft 14 can be moved further in a distal direction away from the hand piece 12 (FIG. 1). Further distal movement of the outer shaft 14 functions to apply additional pressing force onto one or both of the inner jaw members 108, 114. However, because the outer jaw members 106, 112 are already in the first closed configuration, the additional pressing force applied onto one or both of the inner jaw members 108, 114 functions to cause one or both of the opposing inner jaw members 108, 114 to move towards each other and/or towards the axis 20. In other words, one or both of the elements 110, 116 expand or stretch, which therefore causes one or both of the inner jaw member 108, 114 to move away from the respective outer jaw member 106, 112 and closer towards one another and/or the axis 20 so that the effecting surfaces 128, 132 contact the anatomical feature A, and/or apply a greater clamping force onto the anatomical feature A than the clamping force applied by the effecting surface 128, 132 when the jaw assembly 100 is in the first closed configuration C1 (FIG. 5).

When the jaw assembly is in the second closed configuration C2, the effecting surface 126 of the first outer jaw member 106 is generally aligned with, flush with, or located or arranged on a common plane with the effecting surface 128 of the first inner jaw member 108. In the second closed configuration C2, the effecting surface 130 of the second outer jaw member 112 is generally aligned with, flush with, or located or arranged on a common plane with the effecting surface 132 of the second inner jaw member 114.

In an operation during movement of the jaw assembly 100 into the second closed configuration C2, or in an operation after the jaw assembly 100 has been moved in the second closed configuration C2, the anatomical feature can be cut or effected with a cut blade (e.g., see cut blade 200, FIG. 5); a fluid can be provided onto the anatomical feature (FIG. 5); and/or a therapy current can be applied onto the anatomical feature from one or more portions of the jaw assembly that are in electrical communication with the power source (FIG. 1).

By moving the outer member 14 proximally towards the hand piece, the pressing force applied onto one or both of the inner jaw members 108, 114 is reduced or eliminated, which allows the jaws 102, 104 to move or pivot about the respective pivot joints 120, 118 and 124, 122 so that the jaw assembly 100 is moved into either the first closed configuration or into the open configuration O illustrated in FIG. 2. Moving the outer shaft 14 proximally towards the hand piece while the jaw assembly 100 is in the first closed configuration may function to move the jaw assembly 100 into the open configuration illustrated in FIG. 3.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

LISTING OF REFERENCE NUMERALS 10 medical instrument
12 hand piece
14 outer shaft
16 inner shaft
18 longitudinal axis
19 axis or plane
20 axis or plane 22 user control—lever
24 user control—trigger
26 user control—wheel
28 user control—button
30 power source
32 fluid source
100 jaw assembly
102 first jaw
104 second jaw
106 first outer jaw member
108 first inner jaw member
110 element connecting the first outer jaw member 106 and the first inner jaw member 108
112 second outer jaw member
114 second inner jaw member
116 element connecting second outer jaw member 112 and second inner jaw member 114
118 pivot joint—first inner jaw member 108 and inner shaft 16
120 pivot joint—first inner jaw member 108 and outer shaft 14
122 pivot joint—second inner jaw member 114 and inner shaft 16
124 pivot joint—second inner jaw member 114 and outer shaft 14
126 effecting surface—first outer jaw member 106
128 effecting surface—first inner jaw member 108
130 effecting surface—second outer jaw member 112
132 effecting surface—second inner jaw member 114
134 distal—most end of first outer jaw member 106
136 distal—most end of first inner jaw member 108
138 distal—most end of second outer jaw member 112
140 distal—most end of second inner jaw member 114
200 cut blade
202 distal end of cut blade
204 weep hole
O open configuration
C1 first closed configuration
C2 second closed configuration
A anatomical feature
F fluid

The invention claimed is:

1. A jaw assembly comprising:
   a first jaw comprising: a first outer jaw member having an effecting surface, a first inner jaw member having an effecting surface, and an element connecting the first outer jaw member and the first inner jaw member, the first inner jaw member is moveable relative to the first outer jaw member; and
   a second jaw;
   wherein the effecting surface of the first outer jaw member is proud of the effecting surface of the first inner jaw member in a direction of the second jaw.

2. The jaw assembly according to claim 1, wherein the element is a biasing member that is configured to pull the first inner jaw member in a direction of the first outer jaw member when the jaw assembly is in an open configuration such that in the open configuration, the effecting surface of the first outer jaw member is proud of the effecting surface of the first inner jaw member in the direction of the second jaw.

3. The jaw assembly according to claim 1, wherein the element is a tension spring.

4. The jaw assembly according to claim 1, wherein the effecting surface of the first outer jaw member is distal of the effecting surface of the first inner jaw member.

5. The jaw assembly according to claim 1, wherein the jaw assembly is moveable into a first closed configuration where the first outer jaw member is moved towards the second jaw and configured to apply a first gripping force onto an anatomical feature provided between the first jaw and the second jaw, and
   wherein in the first closed configuration, the effecting surface of the first outer jaw member is proud of the effecting surface of the first inner jaw member in the direction of the second jaw.

6. The jaw assembly according to claim 5, wherein the jaw assembly is moveable into a second closed configuration where the first inner jaw member is moved relative to the first outer jaw member in the direction of the second jaw and configured to apply a second gripping force onto the anatomical feature.

7. The jaw assembly according to claim 6, wherein in the second closed configuration, the effecting surface of the first outer jaw member is generally flush with the effecting surface of the first inner jaw member.

8. The jaw assembly according to claim 6, wherein in the element is configured to expand during movement of the jaw assembly into the second closed configuration so that the first inner jaw member moves relative to the first outer jaw member.

9. The jaw assembly according to claim 1, wherein the second jaw comprises: a second outer jaw member, a second inner jaw member, and an element connecting the second outer jaw member, and the second inner jaw member such that the second inner jaw member is moveable relative to the second outer jaw member.

10. The jaw assembly according to claim 9, wherein the second outer jaw member comprises an effecting surface and the second inner jaw member comprises an effecting surface,
    wherein the effecting surface of the second outer jaw member is proud of the effecting surface of the second inner jaw member in a direction of the first jaw.

11. A medical device comprising the jaw assembly according to claim 1, wherein the medical device comprises a cut blade that is located in between the first jaw and the second jaw.

12. The medical device according to claim 11, wherein the cut blade comprises a weep port that is in communication with a fluid source, and fluid from the fluid source is configured to be delivered through the weep port.

13. A medical device comprising the jaw assembly according to claim 1, wherein the medical device comprises an inner shaft located within an outer shaft, and
    wherein the first inner jaw member is connected to the inner shaft.

14. The medical device according to claim 13, wherein proximal movement of the outer shaft relative to the inner shaft is configured to move the jaw assembly into an open configuration, and
    wherein in the open configuration, the effecting surface of the first outer jaw member is proud of the effecting surface of the first inner jaw member in the direction of the second jaw.

15. The medical device according to claim 13, wherein distal movement of the outer shaft relative to the inner shaft is configured to move the jaw assembly into a closed configuration, and
    wherein in the closed configuration, the effecting surface of the first outer jaw member is proud of the effecting surface of the first inner jaw member in the direction of the second jaw.

16. The medical device according to claim 15, wherein further distal movement of the outer shaft relative to the inner shaft is configured to move the jaw assembly into a second closed configuration, and wherein in the second closed configuration, the effecting surface of the first outer jaw member is generally flush with the effecting surface of the first inner jaw member in the direction of the second jaw.

17. The medical device according to claim 16, wherein during the further distal movement of the outer shaft relative to the inner shaft, the element is stretched so that the first inner jaw member is moved in the direction of the second jaw.

18. A method of treating an anatomical feature with the jaw assembly according to claim 1, wherein the method comprises:

moving the jaw assembly into a first closed position so that a first gripping force is applied onto the anatomical feature with the effecting surface of the first outer jaw member and the second jaw;

moving a cut blade to cut the anatomical feature and/or deliver a fluid to the anatomical feature;

moving the jaw assembly into a second closed position so that a second gripping force is applied onto the anatomical feature with the effecting surface of the first inner jaw member and the second jaw; and electrically effecting the anatomical feature with the effecting surface of the first inner jaw member and/or with the effecting surface of the first outer jaw member;

wherein in both an open configuration and the first closed configuration, the effecting surface of the first outer jaw member is proud of the effecting surface of the first inner jaw member in the direction of the second jaw.

19. A jaw assembly comprising:

a first jaw comprising: a first outer jaw member having an effecting surface, a first inner jaw member having an effecting surface, and an element connecting the first outer jaw member and the first inner jaw member, the first inner jaw member is moveable relative to the first outer jaw member; and a second jaw;

wherein the effecting surface of the first outer jaw member is laterally proud of the effecting surface of the first inner jaw member.

20. A jaw assembly comprising:

a first jaw comprising: a first outer jaw member having an effecting surface, a first inner jaw member having an effecting surface, and a first coil spring connecting the first outer jaw member and the first inner jaw member such that the first inner jaw member is moveable relative to the first outer jaw member; and a second jaw comprising: a second outer jaw member having an effecting surface, a second inner jaw member having an effecting surface, and a second coil spring connecting the second outer jaw member and the second inner jaw member such that the second inner jaw member is moveable relative to the second outer jaw member;

wherein the effecting surface of the first outer jaw member is distal of the effecting surface of the first inner jaw member;

wherein the effecting surface of the first outer jaw member is proud of the effecting surface of the first inner jaw member in a direction of the second jaw;

wherein the effecting surface of the second outer jaw member is distal of the effecting surface of the second inner jaw member; and wherein the effecting surface of the second outer jaw member is proud of the effecting surface of the second inner jaw member in a direction of the first jaw.

* * * * *